US007541142B2

(12) United States Patent
Kennedy

(10) Patent No.: US 7,541,142 B2
(45) Date of Patent: *Jun. 2, 2009

(54) PANCREATIC CANCER GENES

(75) Inventor: Giulia C. Kennedy, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/351,953

(22) Filed: Jan. 24, 2003

(65) Prior Publication Data

US 2003/0212264 A1 Nov. 13, 2003

Related U.S. Application Data

(60) Continuation of application No. 09/773,459, filed on Jan. 31, 2001, now Pat. No. 6,664,054, which is a division of application No. 09/337,171, filed on Jun. 21, 1999, now Pat. No. 6,262,249.

(60) Provisional application No. 60/090,391, filed on Jun. 23, 1998, provisional application No. 60/118,570, filed on Feb. 3, 1999.

(51) Int. Cl.
C12Q 1/68 (2006.01)
C12P 19/34 (2006.01)
C07H 21/02 (2006.01)
C07H 21/04 (2006.01)

(52) U.S. Cl. .......................... 435/6; 435/91.1; 536/23.1; 536/24.3

(58) Field of Classification Search ............ 435/6, 435/91.1, 91.31, 455, 458; 514/44; 536/23.1, 536/24.5, 24.3
See application file for complete search history.

(56) References Cited

U.S. PATENT DOCUMENTS

| 4,843,019 | A | 6/1989 | Escribano-Crespo et al. |
| 5,645,994 | A | 7/1997 | Huang |
| 6,262,249 | B1 * | 7/2001 | Kennedy ................. 536/24.31 |
| 6,610,906 | B1 * | 8/2003 | Kurachi et al. ............... 800/25 |
| 2004/0241651 | A1 * | 12/2004 | Olek et al. ..................... 435/6 |

FOREIGN PATENT DOCUMENTS

| EP | 376 746 A2 | 7/1990 |
| WO | WO 86/02081 | 4/1986 |
| WO | WO 91/08217 | 6/1991 |
| WO | WO 95/00651 | 1/1995 |
| WO | WO 98/02560 | 1/1998 |
| WO | WO 98/55510 | 12/1998 |
| WO | WO 99/04265 | 1/1999 |
| WO | WO 99/07840 | 2/1999 |
| WO | WO 99/18208 | 4/1999 |

OTHER PUBLICATIONS

Opalinsska, J.B. et al., Natture Reviews, vol. 1, pp. 503-514 92002).*
Branch, A.D., Trends in Biochem. Sci., vol. 23, pp. 45-50 (1998).*
Agrawal, S. et al., Molecular Med. Today, vol. 6, pp. 72-81 (2002).*
Crooke, S.T., Antisense Research & Application, Chapter 1, pp. 1-50, Ed. by S. Crooke, Publ. by Springer-Verlag (1998).*
Chirila, T.V. et al., Biomaterials, vol. 23, pp. 321-342 (2002).*
Peracchi, A., Prospects for antiviral ribozymes and deoxyribozymes, Rev. Med. Virol., vol. 14, pp. 47-64 (2004).*
Genbank Accession No. D25542, 2003.
Genbank Accession No. AC004673 2002.
Genbank Accession No. AL021808, 2001.
Genbank Accession No. L00016, 2000.
Genbank Accession No. S73498, 2000.
Genbank Accession No. AC004842, 1999.
Genbank Accession No. D16919, 1999.
Genbank Accession No. D87953, 1999.
Branch, A., *A Good Antisense Molecule Is Hard To Find*, Trends in Biochemical Sciences, 23:45-50, Feb. 1998.
Crooke, S.T., *Antisense Research and Application*, Stanley Crooke (Ed.), Springer Verlas Publisher, Chapter 1, "Basic Principles of Antisense Therapeutics," pp. 1-50, 1998.
Genbank Accession No. AA775961, 1998.
Genbank Accession No. AA812053, 1998.
Genbank Accession No. AC002509, 1998.
Genbank Accession No. AC004636, 1998.
Genbank Accession No. AC004934, 1998.
Genbank Accession No. U15174, 1998.
Genbank Accession No. X72308, 1998.
Genbank Accession No. A42048, 1997.
Genbank Accession No. AA211581, 1997.
Genbank Accession No. AA285258, 1997.
Genbank Accession No. AA307669 1997.
Genbank Accession No. AA342359 1997.
Genbank Accession No. AA469145, 1997.
Genbank Accession No. AA469432, 1997.
Genbank Accession No. AA514342, 1997.
Genbank Accession No. AA557331, 1997.
Genbank Accession No. AA558219, 1997.
Genbank Accession No. AA575992, 1997.
Genbank Accession No. AA577673, 1997.
Genbank Accession No. AA603037, 1997.
Genbank Accession No. AA618088, 1997.
Genbank Accession No. AA627720, 1997.
Genbank Accession No. AC002488, 1997.

(Continued)

*Primary Examiner*—Jane Zara
(74) *Attorney, Agent, or Firm*—Patricia Tsao; Lisa Alexander

(57) ABSTRACT

The present invention provides the art with the DNA coding sequences of polynucleotides that are up- or down-regulated in cancer and dysplasia. These polynucleotides and encoded proteins or polypeptides can be used in the diagnosis or identification of cancer and dysplasia. Inhibitors of the up-regulated polynucleotides and proteins can decrease the abnormality of cancer and dysplasia. Enhancing the expression of down-regulated polynucleotides or introducing down-regulated proteins to cells can decrease the growth and/or abnormal characteristics of cancer and dysplasia.

9 Claims, No Drawings

OTHER PUBLICATIONS

Genbank Accession No. AF014958, 1997.
Genbank Accession No. U78027, 1997.
Genbank Accession No. AA115451, 1996.
Genbank Accession No. U09716, 1996.
Genbank Accession No. X04106, 1996.
Genbank Accession No. X89832, 1996.
Genbank Accession No. H92133, 1995.
Genbank Accession No. G06825, 1995.
Genbank Accession No. L08048, 1995.
Genbank Accession No. U01925, 1995.
Genbank Accession No. L22569, 1994.
Genbank Accession No. L33404, 1994.
Genbank Accession No. U15977, 1994.
Genbank Accession No. A07400, 1993.
Genbank Accession No. J03799, 1993.
Genbank Accession No. X15005, 1993.
Genbank Accession No. Z19093, 1993.
Genbank Accession No. V00710, 1992.
Genbank Accession No. AC004168.
Creighton et al. "Genes regulated by estrogen in breast tumor cells in vitro are similarly regulated in vivo in tumor xenografts and human breast tumors", *Genome Biology*. vol. 7, 4: R28. Jul. 7, 2006.
McCown et al. "Protection of Mice Against Lethal Japanese Encephalitis with a Recombinant Baculovirus Vaccine", *Am. J. Trop Med. Hyg.* 42(5): 491-499, 1990.

Minn et al. "Genes that mediate breast cancer metastasis to lung", *Nature*, 436 (7050) 518-524, Jul. 28, 2005.
Ree et al. "Regulation of tissue-degrading factors and in vitro invasiveness in progression of breast cancer cells," *Clin. Exp. Metastasis.* 16:205-215, 1998.
Rueda et al. "Effect of Different Baculovirus Inactivation Procedures on the Integrity and Immunogenicity of Porcine Parvovirus-like Particles", *Vaccine*, (19)726-734, 2001.
Tai et al. "Differential Expression of Metallothionein 1 and 2 Isoforms in Breast Cancer Lines with Different Invasive Potential", *American Journal of Pathology*, vol. 163:5. Nov. 2003.
Tockman et al., "Prospective Detection of Preclinical Lung Cancer: Results from Two Studies of Heterogeneous Nuclear Ribonucleoprotein A2/B1 Overexpression," *Clinical Cancer Research*, vol. 3 2237-2246, Dec. 1997.
Tockman et al., "Considerations in Bringing a Cancer Biomarker to Clinical Application", *Cancer Research*. 52, 2711-2718, May 1, 1992.
Weightman et al. "Photochemical Inactivation of Recombinant Baculovirus", *Journal of Virological Methods* (81)179-182, 1999.
Wistuba et al. "Comparison of Features of Human Breast Cancer Cell Lines and Their Corresponding Tumors", *Clinical Cancer Research*, vol. 4, 2931-2938, Dec. 1998.

* cited by examiner

PANCREATIC CANCER GENES

This application claims priority to provisional applications Ser. No. 60/090,391, filed Jun. 23, 1998, and Ser. No. 60/118,570, filed Feb. 3, 1999.

TECHNICAL AREA OF THE INVENTION

The invention relates to the area of diagnosis and treatment of pancreatic cancer and dysplasia. More specifically, it relates to polynucleotides which are differentially regulated in pancreatic cancer and dysplasia.

BACKGROUND OF THE INVENTION

Pancreatic cancer is the fifth leading cause of cancer death in the United States. According to the American Cancer Society, approximately 28,000 people will die of pancreatic cancer in the United States in 1998. A high risk of developing pancreatic cancer, without a corresponding increase in the risk of developing other cancers, may be passed along in some families. Pancreatic cancer is most likely caused by an accumulation of mutations in specific cancer-causing genes. Pancreatic cancer is very aggressive and chemotherapeutic agents which may be active against other malignancies do not work effectively when used for pancreatic cancer.

The majority of cells in the pancreas are in the exocrine glands, which produce pancreatic enzymes, and in the ducts that carry the pancreatic enzymes to the bile duct and to the small intestine. Cancers of the exocrine cells of the pancreas are usually adenocarcinomas. Pancreatic adenocarcinomas usually begin in the ducts of the pancreas, but may sometimes develop from the acinar cells. About 95% of cancers of the pancreas are adenocarcinomas. Less common cancers of the exocrine pancreas include adenosquamous carcinomas, squamous cell carcinomas, and giant cell carcinomas.

Because pancreatic cancer is an aggressive cancer with very high mortality, there is a need in the art for genes that are up- or down-regulated in tumor progression. Such genes are useful for therapeutic purposes and for diagnosis of pancreatic as well as other cancers.

SUMMARY OF THE INVENTION

The invention provides isolated polynucleotides comprising coding regions or portions of genes whose expression is mis-regulated in cancer and dysplasia.

The invention also provides isolated proteins and protein fragments whose expression is mis-regulated in cancer and dysplasia.

The invention further provides an antibody preparation which specifically binds to a polypeptide the expression of which is mis-regulated in cancer and dysplasia.

The invention provides a method for diagnosing cancer and dysplasia.

The invention still further provides therapeutic compositions useful for treating cancer and dysplasia.

These and other objects of the invention are provided by one or more of the embodiments described below. One embodiment of the invention provides isolated polynucleotides comprising at least twelve contiguous nucleotides selected from the group of polynucleotide sequences as shown in SEQ ID NOs:1-15.

Another embodiment of the invention provides isolated polypeptides comprising at least six contiguous amino acids encoded by a polynucleotide selected from the group consisting of the polynucleotide sequences as shown in SEQ ID NOs:1-15.

Even another embodiment of the invention provides an antibody preparation which specifically binds to a polypeptide comprising at least six contiguous amino acids encoded by a polynucleotide selected from the group of polynucleotide sequences as shown in SEQ ID NOs:1-15.

Yet another embodiment of the invention provides isolated nucleotide probes consisting of a sequence selected from the group consisting of the polynucleotide sequences shown in SEQ ID NOs:1-15.

Still another embodiment of the invention provides a method of diagnosing cancer. The amount of a polypeptide expressed from a polynucleotide having a sequence as shown in SEQ ID NO:12 in a test sample of tissue of a human suspected of being cancerous is determined. The amount of said polypeptide is also determined in a human tissue which is normal. The determined amounts are then compared. A test sample which contains less of the polypeptide than the normal tissue is identified as cancerous.

A further embodiment of the invention provides an additional method of diagnosing cancer. The amount of specific mRNA molecules in a test sample of tissue suspected of being cancerous and in a human tissue which is normal are determined. The mRNA molecules to be measured are complementary to the minus strand of a double-stranded polynucleotide sequence. The double-stranded polynucleotide sequence is shown in SEQ ID NO:12. The determined amounts of mRNA molecules are compared. A test sample of tissue which contains less of the mRNA molecules than the normal tissue is identified as cancerous.

Another embodiment of the invention provides a therapeutic composition useful for reducing the growth rate of cancer cells The composition is comprised of a polynucleotide comprising all or a portion of a nucleotide sequence which is operably linked to a promoter sequence and a pharmaceutically acceptable carrier. The polynucleotide comprising all or a portion of a nucleotide sequence comprises at least 18 contiguous nucleotides. The nucleotide sequence is shown in SEQ ID NO:12.

Yet another embodiment of the invention provides a therapeutic composition useful for reducing the growth rate of cancer cells. The composition is comprised of a polypeptide comprising all or a portion of an amino acid sequence expressed from a polynucleotide sequence and a pharmaceutically acceptable carrier. The polynucleotide sequence is shown in SEQ ID NO:12.

Another embodiment of the invention provides a method of diagnosing dysplasia and cancer. The amount of a polypeptide expressed from a polynucleotide having at least one of a sequence selected from the group consisting of the polynucleotide sequences shown in SEQ ID NOs:2, 5, and 15 in a test sample of tissue suspected of being dysplastic or cancerous is determined. The amount of the polypeptide is also determined in a human tissue which is normal. The determined amounts are compared. A test sample of human tissue which contains more of at least one polypeptide than the normal tissue is identified as being dysplastic or cancerous.

A further embodiment of the invention provides another method of diagnosing dysplasia. The amount of a polypeptide expressed from a polynucleotide having a sequence selected from the group consisting of the polynucleotide sequences shown in SEQ ID NOs:1, 3-4, 6-11, and 13-14 is determined in a test sample of tissue suspected of being dysplastic. The amount of said polypeptide is also determined in a human tissue which is normal The two amounts are then compared.

A test sample of human tissue which contains more of said polypeptide than the normal tissue is identified as being dysplastic.

Another embodiment of the invention provides an additional method of diagnosing cancer.

The amount of a polypeptide expressed from a polynucleotide having a sequence selected from the group consisting of the polynucleotide sequences shown in SEQ ID NOs:2, 5, and 15, is determined in a test sample of tissue suspected of containing cancer, and in a human tissue which is normal. The amount of a polypeptide expressed from a polynucleotide having a sequence selected from the group consisting of the polynucleotide sequences shown in SEQ ID NOs:1, 3-4, 6-11, and 13-14 is also determined in the test sample, and in the normal tissue. The determined amounts of said polypeptides are then compared. A test sample of tissue which contains more of the polypeptide expressed from a polynucleotide having a sequence selected from the group consisting of the polynucleotide sequences shown in SEQ ID NOs:2, 5, and 15, as compared to the normal tissue, and which contains substantially the same amount of a polypeptide expressed from a polynucleotide selected from the group as shown in SEQ ID NOs:1, 3-4, 6-11, and 13-14, as compared to the normal tissue, is identified as cancerous.

Even another embodiment of the invention provides a method of diagnosing dysplasia and cancer. The amount of specific mRNA molecules is determined in a test sample of tissue suspected of being dysplastic or cancerous and in a human tissue which is normal. The mRNA molecules measured are complementary to the minus strand of a double-stranded polynucleotide sequence. The double-stranded polynucleotide sequence is selected from the group of polynucleotides as shown in SEQ ID NOs:2, 5, and 15. The determined amounts of mRNA molecules are compared. A test sample of human tissue which contains more of the mRNA molecules than the normal tissue is identified as being dysplastic or cancerous.

Yet another embodiment of the invention provides a method of diagnosing dysplasia. The amounts of specific mRNA molecules in a test sample of human tissue suspected of being dysplastic and in a human tissue which is normal are determined. The mRNA molecules are complementary to the minus strand of a double-stranded polynucleotide sequence. The double-stranded polynucleotide sequence is selected from the group of polynucleotides as shown in SEQ ID NOs: 1, 3-4, 6-11, and 13-14. The determined amounts of mRNA molecules are then compared. A test sample of human tissue which contains more of the mRNA molecules than the normal tissue is identified as being dysplastic.

Still another embodiment of the invention provides a method of diagnosing cancer. The amounts of a first set of specific mRNA molecules in a test sample of tissue of a human suspected of being cancerous and in a human tissue which is normal are determined. The mRNA molecules are complementary to the minus strand of a double-stranded polynucleotide sequence. The double-stranded polynucleotide sequence is selected from the group of polynucleotide sequences as shown in SEQ ID NOs:1, 3-4, 6-11, and 13-14. In addition, the amounts of a second set of specific mRNA molecules in a test sample of tissue of a human suspected of being cancerous and in a human tissue which is normal are determined. The mRNA molecules are complementary to the minus strand of a double-stranded polynucleotide sequence. The double-stranded polynucleotide sequence is selected from the group of polynucleotide sequences as shown in SEQ ID NOs:2, 5, and 15. The determined amounts of the first and second sets of mRNA molecules are compared. A test sample of human tissue which contains more of the second set of mRNA molecules than the normal tissue, and which contains substantially the same amount of the first set of mRNA molecules, as compared to the normal tissue, is identified as cancerous.

Yet another embodiment of the invention provides a therapeutic composition useful for decreasing the amount of translation of an RNA molecule in a cell. The composition comprises an antisense polynucleotide complementary to the plus strand of a double-stranded polynucleotide. The double-stranded polynucleotide is selected from the group consisting of polynucleotides comprising a nucleotide sequence as shown in SEQ ID NOs:1-11, and 13-15, wherein said antisense polynucleotide binds to an mRNA molecule. The composition also includes a pharmaceutically acceptable carrier.

A further embodiment of the invention provides a therapeutic composition useful for reducing the expression of a polypeptide. The composition comprises an antibody which specifically binds to a polypeptide expressed from a polynucleotide selected from the group consisting of polynucleotides comprising a nucleotide sequence as shown in SEQ ID NOs:1-11 and 13-15. The composition also includes a pharmaceutically acceptable carrier.

Another embodiment of the invention provides a therapeutic composition useful for reducing the translation from an mRNA molecule. The composition comprises a ribozyme which binds to an mRNA molecule, wherein a portion of said ribozyme is complementary to the plus strand of a double-stranded polynucleotide. The polynucleotide is selected from the group consisting of the polynucleotides comprising a sequence as shown in SEQ ID NOs:1-11, and 13-15. The composition also comprises a pharmaceutically acceptable carrier The present invention provides the art with useful polynucleotides which represent expressed sequences of genes. Expression of the genes is mis-regulated in cancer. The invention also provides the art with diagnostic methods based on the over- and under-expression of the genes and the polypeptides encoded by the genes in cancer and dysplastic cells Inhibitors of the over-expressed polynucleotides and polypeptides can be used to reduce the growth of cancer cells and dysplastic cells. The polynucleotides and polypeptides which are under-expressed in cancer and dysplasia can be delivered therapeutically to reduce the abnormal characteristics of cancer cells and dysplastic cells.

DETAILED DESCRIPTION OF THE PREFERRED EMBODIMENTS

Polynucleotides that are mis-regulated in cancer and dysplasia are disclosed. The mis-regulated polynucleotide sequences are shown in SEQ ID NOs:1-15. The polynucleotides are mis-regulated as follows:

SEQ ID NO:12 is down-regulated in cancer;

SEQ ID NOs:2, 5, and 15 are up-regulated in cancer and dysplasia, and

SEQ ID NOs:1, 3-4, 6-11, and 13-14 are up-regulated in dysplasia only.

Polynucleotides that are differentially regulated in cancer or dysplasia or both can be useful in the diagnosis and treatment of these diseases. Dysplasia is an atypical proliferation of epithelial or mesenchymal cells that may represent an early stage of cancer; however, dysplasia does not necessarily progress to cancer Epithelial dysplasia results in the loss of normal orientation of one epithelial cell to another, accompanied by alterations in cellular and nuclear size and shape.

Cancer is a proliferation of malignant cells that are no longer under normal physiologic control.

The subgenomic polynucleotides of the invention contain less than a whole chromosome and are preferably intron-free. The subgenomic polynucleotides of the invention can be isolated and purified free from other nucleotide sequences by standard nucleic acid purification techniques, for example, using PCR, cloning, and/or restriction enzymes and probes to isolate fragments comprising the encoding sequences. Subgenomic polynucleotides of the invention can include all or a contiguous portion of a gene coding region. In one embodiment, an isolated and purified subgenomic polynucleotide of the invention comprises at least 10, 11, 12, 15, 18, 20, 25, 30, 35, 40, 45, 50, 60, 70, 74, 80, 90, 100, 125, 150, 154, 175, 200, 250, 300, or 350 contiguous nucleotides selected from the polynucleotide sequences as shown in SEQ ID NOs:1-15. In a preferred embodiment, the polynucleotide molecules comprise a contiguous sequence of at least twelve nucleotides selected from the group consisting of the polynucleotides shown in SEQ ID NOs:1-15.

An open reading frame is a region of DNA that consists exclusively of triplets that represent amino acids. The open reading frame of the polynucleotide sequences of the invention can be determined by examining all three possible reading frames in both directions. If a reading frame contains termination codons it cannot be read into protein and is not considered an open reading frame. Usually, no more than one of the six possible frames is open in any single stretch of DNA. An extensive open reading frame is unlikely to exist by chance because of the lack of selective pressure to prevent the accumulation of nonsense codons. Therefore, the identification of a lengthy open reading frame is taken to be prima facie evidence that the sequence is translated into protein in that frame. Lewin, ed,. 1990, *Genes IV*, Cell Press, Cambridge, Mass.

Subgenomic polynucleotides of the invention can be used, initer alia, to produce proteins or polypeptides, as probes for the detection of mRNA of the invention in samples or extracts of human cells, to generate additional copies of the polynucleotides, and to generate ribozymes or antisense oligonucleotides. The subgenomic polynucleotides can also be used as single stranded DNA probes or as triple-strand forming oligonucleotides. The probes can be used to determine the presence or absence of the polynucleotide sequences as shown in SEQ ID NOs:1-15 or variants thereof in a sample.

The sequence of a nucleic acid comprising at least 15 contiguous nucleotides of at least any one of SEQ ID NO:1-15, preferably the entire sequence of at least any one of SEQ ID NO:1-15, is not limited and can be any sequence of A, T, G, and/or C (for DNA) and A, U, G, and/or C (for RNA) or modified bases thereof, including inosine and pseudouridine. The choice of sequence will depend on the desired function and can be dictated by coding regions desired, the intron-like regions desired, and the regulatory regions desired.

Where the entire sequence of any one of SEQ ID NO:1-15 is within the nucleic acid, the nucleic acid obtained is referred to herein as a polynucleotide comprising the sequence of any one of SEQ ID NO:1-15.

Both secreted and membrane-bound polypeptides of the present invention are of interest. For example, levels of secreted polypeptides can be assayed conveniently in body fluids, such as blood and urine. Membrane-bound polypeptides are useful for constructing vaccine antigens or inducing an immune response. Such antigens would comprise all or part of the extracellular region of the membrane-bound polypeptides.

Because both secreted and membrane-bound polypeptides comprise a fragment of contiguous hydrophobic amino acids, hydrophobicity predicting algorithms can be used to identify such polypeptides.

A signal sequence is usually encoded by both secreted and membrane-bound polypeptide genes to direct a polypeptide to the surface of the cell. The signal sequence usually comprises a stretch of hydrophobic residues. Such signal sequences can fold into helical structures.

Membrane-bound polypeptides typically comprise at least one transmembrane region that possesses a stretch of hydrophobic amino acids that can transverse the membrane. Some transmembrane regions also exhibit a helical structure.

Hydrophobic fragments within a polypeptide can be identified by using computer algorithms. Such algorithms include Hopp & Woods, *Proc. Natl. Acad. Sci. USA* 78:3824-3828 (1981); Kyte & Doolittle, *J. Mol. Biol.* 157:105-132 (1982), and RAOAR algorithm, Degli Esposti et al. *Eur J. Biochem.* 190:207-219 (1990).

Another method of identifying secreted and membrane-bound polypeptides is to translate the present polynucleotides, SEQ ID NO:1-15, in all six frames and determine if at least 8 contiguous hydrophobic amino acids are present. Those translated polypeptides with at least 8; more typically, 10, even more typically, 12 contiguous hydrophobic amino acids are considered to be either a putative secreted or membrane bound polypeptide. Hydrophobic amino acids include alanine, glycine, histidine, isoleucine, leucine, lysine, methionine, phenylalanine, proline, threonine, tryptophan, tyrosine, and valine.

The polypeptides of the invention include those encoded by the disclosed polynucleotides. These polypeptides can also be encoded by nucleic acids that, by virtue of the degeneracy of the genetic code, are not identical in sequence to the disclosed polynucleotides. Thus, the invention includes within its scope nucleic acids comprising polynucleotides encoding a protein or polypeptide expressed by a polynucleotide having the sequence of any one of SEQ ID NO:1-15. Also within the scope of the invention are variants, variants of polypeptides include mutants, fragments, and fusions. Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. For example, substitutions between the following groups are conservative: Gly/Ala, Val/Ile/Leu, Asp/Glu, Lys/Arg, Asn/Gln, Ser/Cys,Thr, and Phe/Trp/Tyr.

Cysteine-depleted muteins are variants within the scope of the invention. These variants can be constructed according to methods disclosed in U.S. Pat. No. 4,959,314, "Cysteine-Depleted Muteins of Biologically Active Proteins." The patent discloses how to substitute other amino acids for cysteines, and how to determine biological activity and effect of the substitution. Such methods are suitable for proteins according to this invention that have cysteine residues suitable for such substitutions, for example to eliminate disulfide bond formation.

The protein variants described herein are encoded by polynucleotides that are within the scope of the invention. The genetic code can be used to select the appropriate codons to construct the corresponding variants.

The invention encompasses polynucleotide sequences having at least 65% sequence identity to any one of SEQ ID NOs:1-15 as determined by the Smith-Waterman homology search algorithm as implemented in MSPRCH program (Oxford Molecular) using an affine gap search with the following search parameters: gap open penalty of 12, and gap extension penalty of 1.

Polynucleotide probes comprising at least 12 contiguous nucleotides selected from the nucleotide sequence of a polynucleotide of SEQ ID NO:1-15 are used for a variety of purposes, including identification of human chromosomes and determining transcription levels.

The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art A nucleotide probe will hybridize specifically to nucleotide sequences in the chromosome preparations which are complementary to the nucleotide sequence of the probe. A probe that hybridizes specifically to a polynucleotide should provide a detection signal at least 5-, 10-, or 20-fold higher than the background hybridization provided with other unrelated sequences.

Polynucleotides of the present invention are used to identify a chromosome on which the corresponding gene resides. Using fluorescence in situ hybridization (FISH) on normal metaphase spreads, comparative genomic hybridization allows total genome assessment of changes in relative copy number of DNA sequences. See Schwartz and Samad, *Current Opinions in Biotechnology* (1994) 8:70-74; Kallioniemi et al., *Seminars in Cancer Biology* (1993) 4:41-46, Valdes and Tagle, *Methods in Molecular Biology* (1997) 68:1, Boultwood, ed., Human Press, Totowa, N.J.

Preparations of human metaphase chromosomes are prepared using standard cytogenetic techniques from human primary tissues or cell lines. Nucleotide probes comprising at least 12 contiguous nucleotides selected from the nucleotide sequence of SEQ ID NOs:1-15 are used to identify the corresponding chromosome. The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations that are complementary to the nucleotide sequence of the probe. A probe that hybridizes specifically to a polynucleotide-related gene provides a detection signal at least 5-, 10-, or 20-fold higher than the background hybridization provided with non-polynucleotide coding sequences.

Polynucleotides are mapped to particular chromosomes using, for example, radiation hybrids or chromosome-specific hybrid panels. See Leach et. al., *Advances in Genetics*, (1995) 33:63-99; Walter et al., *Nature Genetics* (1994) 7:22-28; Walter and Goodfellow, *Trends in Genetics* (1992) 9:352. Such mapping can be useful in identifying the function of the polynucleotide-related gene by its proximity to other genes with known function. Function can also be assigned to the related gene when particular syndromes or diseases map to the same chromosome.

A polynucleotide will be useful in forensics, genetic analysis, mapping, and diagnostic applications if the corresponding region of a gene is polymorphic in the human population. A particular polymorphic form of the polynucleotide may be used to either identify a sample as deriving from a suspect or rule out the possibility that the sample derives from the suspect. Any means for detecting a polymorphism in a gene are used, including but not limited to electrophoresis of protein polymorphic variants, differential sensitivity to restriction enzyme cleavage, and hybridization to an allele-specific probe.

Any naturally occurring variants of the nucleotide sequences which encode variants thereof are within the scope of this invention. Allelic variants of subgenomic polynucleotides of the invention can occur and can be identified by hybridization of putative allelic variants with nucleotide sequences disclosed herein under stringent conditions. For example, by using the following wash conditions—2×SCC, 0.1% SDS, room temperature twice, 30 minutes each, then 2×SCC, 0.1% SDS, 50° C. once, 30 minutes, then 2×SCC, room temperature twice, 10 minutes each—allelic variants of the polynucleotides of the invention can be identified which contain at most about 25-30% base pair mismatches. More preferably, allelic variants contain 15-25% base pair mismatches, even more preferably 5-15%, or 2-5%, or 1-2% base pair mismatches.

Amplification by the polymerase chain reaction (PCR) can be used to obtain the polynucleotides of the invention, using either genomic DNA or cDNA as a template. The polynucleotides of the invention may also be obtained using reverse transcriptase and mRNA molecules that are complementary to the minus strand of a double-stranded sequence wherein said double-stranded sequence is selected from the group of polynucleotides comprising a sequence as shown in SEQ ID NOs:1-15. Using the polynucleotide sequences disclosed herein, subgenomic polynucleotide molecules of the invention can also be made using the techniques of synthetic chemistry.

Probes specific to the polynucleotides of the invention may be generated using the polynucleotide sequences disclosed in SEQ ID NOS:1-15. The probes are preferably at least 12, 14, 16, 18, 20, 22, 24, or 25 nucleotides in length and can be less than 2, 1, 0.5, 0.1, or 0.05 kb in length. The probes can be synthesized chemically or can be generated from longer polynucleotides using restriction enzymes. The probes can be labeled, for example, with a radioactive, biotinylated, or fluorescent tag.

Subgenomic polynucleotides of the invention can be propagated in vectors and cell lines using techniques well known in the art. Expression systems in bacteria include those described in Chang et al., *Nature* (1978) 275: 615, Goeddel et al., *Nature* (1979) 281: 544; Goeddel et al, *Nucleic Acids Res.* (1980) 8: 4057, EP 36,776; U.S. Pat. No. 4,551,433, deBoer et al. *Proc. Natl. Acad. Sci. USA* (1983) 80: 21-25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol* (1983) 153: 163; Kurtz et al, *Mol Cell. Biol.* (1986) 6: 142, Kunze et al., *J. Basic Microbiol.* (1985) 25: 141, Gleeson et al, *J. Gen. Microbiol.* (1986) 132: 3459, Roggenkamp et al., *Mol. Gen. Genet.* (1986) 202 :302; Das et al., *J. Bacteriol.* (1984) 158: 1165; De Louvencourt et al., *J. Bacteriol.* (1983) 154: 737, Van den Berg et al., *Bio Technology* (1990) 8: 135; Kunze et al, *J. Basic Microbiol.* (1985) 25: 141; Cregg et al., *Mol. Cell. Biol.* (1985) 5: 3376; U.S. Pat. Nos. 4,837,148, 4,929,555, Beach and Nurse, *Nature* (1981) 300: 706; Davidow et al, *Curr. Genet.* (1985) 10: 380, Gaillardin et al., *Curr. Genet.* (1985) 10: 49, Ballance et al., *Biochem. Biophys. Res. Commun.* (1983) 112: 284-289, Tilburn et al., *Gene* (1983) 26: 205-221, Yelton et al., *Proc. Natl. Acad. Sci. USA* (1984) 81: 1470-1474; Kelly and Hynes, *EMBO J.* (1985) 4: 475479; EP 244,234; and WO 91/00357.

Expression of the subgenomic polynucleotides of the invention in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.); EP 127,839; EP 155,476; Vlak et al., *J Gen. Virol.* (1988) 69: 765-776; Miller et al., *Am. Rev. Microbiol.* (1988) 42:177, Carbonell et al, *Gene* (1988) 73: 409; Maeda et al., *Nature* (1985) 315: 592-594, Lebacq-Verheyden et al., *Mol. Cell. Biol.* (1988) 8: 3129, Smith et al., *Proc. Natl. Acad. Sci. USA* (1985) 82: 8404; Miyajima et al., *Gene* (1987) 58:273; and Martin et al., *DNA* (1988) 7.99. Numerous baculoviral strains and variants and corresponding permissive insect host cells from hosts are described in Luckow et al., *Bio/Technology* (1988) 6: 47-55, Miller et al., in GENETIC ENGINEERING (Setlow, J. K. et al. eds.), Vol. 8 (Plenum Publishing, 1986), pp. 277-279; and Maeda et al., *Nature,* (1985) 315: 592-594.

Mammalian expression of the subgenomic polynucleotides of the invention can be accomplished as described in Dijkema et al., *EMBO J.* (1985) 4: 76; Gorman et al., *Proc. Natl. Acad. Sci. USA* (1982) 79: 6777, Boshart et al., *Cell* (1985) 41: 521, and U.S. Pat. No. 4,399,216. Other features of mammalian expression can be facilitated as described in Ham and Wallace, *Meth. Enz.* (1979) 58: 44; Barnes and Sato, *Anal. Biochem.* (1980) 102: 255, U.S. Pat. Nos. 4,767,704; 4,657,866; 4,927,762; 4,560,655; WO 90/103430; WO 87/00195, and U.S. RE 30,985.

The subgenomic polynucleotides of the invention can be on linear or circular molecules. They can be on autonomously replicating molecules (vectors) or on molecules without replication sequences. They can be regulated by their own or by other regulatory sequences, as is known in the art. The subgenomic polynucleotides of the invention can be introduced into suitable host cells using a variety of techniques which are available in the art, such as transferrin-polycation-mediated DNA transfer, transfection with naked or encapsulated nucleic acids, liposome-mediated DNA transfer, intracellular transportation of DNA-coated latex beads, protoplast fusion, viral infection, electroporation, gene gun, and calcium phosphate-mediated transfection.

The invention provides a method of detecting expression of a polynucleotide in, for example, a biological sample, which can be useful, inter alia, for diagnosing cancer or dysplasia. The basis for this method is the discovery that the polynucleotide sequence(s) as shown in:

SEQ ID NO:12 is down-regulated in cancer,

SEQ ID NOs:2, 5, and 15 are up-regulated in cancer and dysplasia, and

SEQ ID NOs:1, 3-4, 6-11, and 13-14 are up-regulated in dysplasia only.

In patients who have been diagnosed with pancreatic dysplasia or cancer, the detection of levels of the expression products of the polynucleotide sequences of the invention, either mRNA or protein, can be used to diagnose or prognose a disorder, to monitor treatment of the disorder, or to screen agents which affect the disorder.

The expression products of the polynucleotide sequences of the invention, either mRNA or proteins, can be detected in a body sample for diagnosis or prognosis. The body sample can be, for example, a solid tissue or a fluid sample. The patient from whom the body sample is obtained can be healthy or can already be identified as having a condition in which altered expression of a protein of the invention is implicated.

In one embodiment, the body sample is assayed for the level of a protein expressed from a polynucleotide sequence of the invention. The protein could be detected by, for example, antibodies to the proteins. The antibodies can be labeled, for example, with a radioactive, fluorescent, biotinylated, or enzymatic tag and detected directly, or can be detected using indirect immunochemical methods, using a labeled secondary antibody. The presence of the protein can be assayed, for example, in tissue sections by immunocytochemistry, or in lysates, using Western blotting, as is known in the art, The level of the protein in a tissue sample suspected of being cancerous or dysplastic is compared with the level of the protein in a normal tissue. A higher level of the polypeptides expressed from polynulcleotide sequences as shown in SEQ ID NOs:1, 3-4, 6-11, and 13-14 in the suspect tissue, as compared to the normal tissue, indicates the presence of dysplastic cells in the suspect tissue. A higher level of the polypeptides expressed from polynucleotide sequences as shown in SEQ ID NOs:2, 5, and 15 in the suspect tissue, as compared to the normal tissue, indicates the presence dysplastic cells or cancerous cells or both in the suspect tissue. A lower level of the polypeptide expressed from the polynucleotide sequence as shown in SEQ ID NO:12 in the suspect tissue, as compared to the normal tissue, indicates the presence of cancerous cells in the suspect tissue.

Additionally, a differentiation between cancer or dysplasia in a patient's diagnosis can be made. The expression of a polynucleotide sequence of the invention that is up-regulated in dysplastic cells only (i.e., SEQ ID NOs:1, 3-4, 6-11, and 13-14) and the expression of a polynucleotide that is up-regulated in both dysplastic cells and cancerous cells (i.e., SEQ ID NOs:2, 5, and 15) can be used to screen a patient's tissues. If examination of a patient's tissues reveals that there is no up-regulation of a polynucleotide sequence that is up-regulated in dysplastic cells only (i.e., SEQ ID NOs:1, 3-4, 6-11, and 13-14), and that there is up-regulation of a polynucleotide sequence that is up-regulated in both cancerous cells and dysplastic cells (i.e., SEQ ID NOs:2, 5, and 15), then the patient is diagnosed with cancer.

Alternatively, the presence of mRNA expressed from the polynucleotide sequences of the invention in two tissues can be compared mRNA can be detected, for example, by in situ hybridization in tissue sections, by reverse transcriptase-PCR, or in Northern blots containing poly A+ mRNA. One of skill in the art can readily determine differences in the size or amount of mRNA transcripts between two tissues, using Northern blots and nucleotide probes For example, the level of mRNA of the invention in a tissue sample suspected of being cancerous or dysplastic is compared with the expression of the mRNA in a normal tissue. Any methods known in the art for determining the amounts of specific mRNAs can be used A higher level of mRNA expressed from polynucleotide sequences as shown in SEQ ID NOs:1, 3-4, 6-11, and 13-14 in the suspect tissue, as compared to the normal tissue, indicates the presence dysplastic cells in the suspect tissue. A higher level of mRNA expressed from the polynucleotide sequences as shown in SEQ ID NOs.2, 5, and 15 in the suspect tissue, as compared to the normal tissue, indicates the presence dysplastic cells or cancerous cells or both in the suspect tissue. A lower level of the mRNA expressed from the polynucleotide sequence as shown in SEQ ID NO:12 in the suspect tissue, as compared to the normal tissue, indicates the presence of cancerous cells in the suspect tissue. Any combinations of these sequences can be used to determine a diagnosis.

Optionally, the level of a particular expression product of a polynucleotide sequence of the invention in a body sample can be quantitated. Quantitation can be accomplished, for example, by comparing the level of expression product detected in the body sample with the amounts of product present in a standard curve. A comparison can be made visually or using a technique such as densitometry, with or without computerized assistance. Alternative methods can be used, for example ELISA, western blot, immunoprecipitation, radioimmunoassay, etc. Any method known in the art for detecting and quantitating a particular protein can be used.

Reagents specific for the polynucleotides and polypeptides of the invention, such as antibodies and nucleotide probes, can be supplied in a kit for detecting the presence of an expression product in a biological sample. The kit can also contain buffers or labeling components, as well as instructions for using the reagents to detect and quantify expression products in the biological sample.

Polynucleotide expression in a cell can be increased or decreased, as desired. Polynucleotide expression can be altered for therapeutic purposes, as described below, or can be used to identify and study the role of therapeutic agents in cancer and other diseases.

Decreasing the expression of genes containing sequences selected from the group consisting of the sequences as shown in SEQ ID NOs:1, 3-4, 6-11, and 13-14 is useful, for example, as a therapeutic for altering the abnormal characteristics of dysplastic cells. Decreasing the expression of polynucleotide sequences selected from the group consisting of the sequences as shown in SEQ ID NOs:2, 5, and 15 is useful, for example, as a therapeutic agent for decreasing the growth rate of dysplastic and cancer cells.

Expression of the polynucleotide sequences of the invention can be altered using an antisense oligonucleotide sequence. Therapeutic compositions for decreasing gene expression comprise an expression construct containing polynucleotides encoding all or a portion of a polynucleotide sequence selected from the group consisting of SEQ ID NOs: 1-11, and 13-15. Within the expression construct, the polynucleotide segment is orientated in the antisense direction and is located downstream from a promoter. Transcription of the polynucleotide segment initiates at the promoter.

Preferably, the antisense oligonucleotide sequence is at least ten nucleotides in length, but longer sequences of at least 11, 12, 15, 20, 25, 30, 35, 40, 45, 50, 60, 70, 74, 80, 90, 100, 125, 150, 162, 175, 200, 250, 300, or 350 contiguous nucleic acids can also be used. Antisense oligonucleotide molecules can be provided in a DNA construct and introduced into cells whose division is to be decreased, as described above. A more complete description of gene transfer vectors, especially retroviral vectors is contained in U.S. Ser. No. 08/869,309, which is incorporated herein by reference.

The antisense oligonucleotides can be composed of deoxyribonucleotides, ribonucleotides, or a combination of both. Oligonucleotides can be synthesized manually or by an automated synthesizer, by covalently linking the 5' end of one nucleotide with the 3' end of another nucleotide with phosphodiester or non-phosphodiester internucleotide linkages such as alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1-8; Sonveaux, 1994, *Meth. Mol. Biol.* 26:1-72; Uhlmann et al., 1990, *Chem. Rev.* 90:543-583.

Although precise complementarity is not required for successful duplex formation between an antisense molecule and the complementary coding sequence of a gene, antisense molecules with no more than one mismatch are preferred. One skilled in the art can easily use the calculated melting point of an antisense-sense pair to determine the degree of mismatch which will be tolerated between a particular antisense oligonucleotide and a particular coding sequence of the selected gene.

The antisense oligonucleotides of the invention can be modified without affecting their ability to hybridize to a polynucleotide coding sequence of the present invention. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases or sugars or both, such as arabinose instead of ribose, or a 3', 5'-substituted oligonucleotide in which the 3' hydroxyl group or the 5' phosphate group are substituted, can also be employed in a modified antisense oligonucleotide These modified oligonucleotides can be prepared by methods well known in the art. Agrawal et al., 1992, *Trends Biotechnol* 10:152-158, Uhlmann et al., 1990, *Chem. Rev.* 90:543-584, Uhlmann et al., 1987, *Tetrahedron. Lett.* 215:3539-3542.

Expression of the polynucleotides of the invention can also be decreased by delivering polyclonal, monoclonal, or single chain antibodies that specifically bind to polypeptides expressed from the polynucleotide sequences as shown in SEQ ID NOs:1-11 and 13-15. Antibodies specific to these proteins bind to the protein and prevent the protein from functioning in the cell. Blocking protein expression or function is useful for preventing, reducing the effects of, or curing cancer and dysplasia.

In one embodiment of the invention, expression of the polynucleotides selected from the group consisting of the polynucleotide sequences shown in SEQ ID NOs:1-11, and 13-15 are decreased using a ribozyme, an RNA molecule with catalytic activity. See, e.g., Cech, 1987, *Science* 236: 1532-1539, Cech, 1990, *Ann. Rev. Biochem.* 59:543-568, Cech, 1992, *Curr. Opin. Struct. Biol.* 2: 605-609; Couture and Stinchcomb, 1996, *Trends Genet.* 12: 510-515. Ribozymes can be used to inhibit gene function by cleaving an RNA sequence, as is known in the art (e.g., Haseloff et al., U.S. Pat. No. 5,641,673).

The coding sequence of a polynucleotide of the invention can be used to generate a ribozyme which will specifically bind to RNA transcribed from said polynucleotide. Methods of designing and constructing ribozymes which can cleave other RNA molecules in trans in a highly sequence specific manner have been developed and described in the art (see Haseloff, J. et al. (1988), *Nature* 334:585-591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach, W. L. et al., EP 321,201). Longer complementary sequences can be used to increase the affinity of the hybridization sequence for the target. The hybridizing and cleavage regions of the ribozyme of the invention can be integrally related, thus, upon hybridizing to the target RNA through the complementary regions, the catalytic region of the ribozyme can cleave the target.

Ribozymes of the invention can be introduced into cells as part of a DNA construct, as is known in the art. The DNA construct can also include transcriptional regulatory elements, such as a promoter element, an enhancer or UAS element, and a transcriptional terminator signal, for controlling the transcription of the ribozyme in the cells.

Mechanical methods, such as microinjection, liposome-mediated transfection, electroporation, gene gun, or calcium phosphate precipitation, can be used to introduce the ribozyme-containing DNA construct into cells whose division it is desired to decrease, as described above. Alternatively, if it is desired that the DNA construct be stably retained by the cells, the DNA construct can be supplied on a plasmid and maintained as a separate element or integrated into the genome of the cells, as is. known in the art, As taught in Haseloff et al U.S. Pat. No. 5,641,673, the ribozymes of the invention can be engineered so that their expression will occur in response to factors which induce expression of a polynucleotides of the invention. The ribozyme can also be engineered to provide an additional level of regulation, so that destruction of RNA occurs only when both the ribozyme and the corresponding gene are induced in the cells.

Preferably, the mechanism used to decrease expression of the polynucleotides of the invention, whether antisense nucleotide sequence, antibody, or ribozyme decreases expression of the polynucleotide by 50%, 60%, 70%, or 80%. Most preferably, expression of the polynucleotide is decreased by 90%, 95%, 99%, or 100%. The effectiveness of the mechanism chosen to alter expression of the polynucleotide can be assessed using methods well known in the art, such as hybridization of nucleotide probes to mRNA of the polynucleotide quantitative RT-PCR, or detection of a protein using specific antibodies of the invention Increased expression of a polynucleotide is useful to decrease the growth rate of cancer cells where the particular polynucleotide is down-regulated in cancer cells, such as the polynucleotide sequence as shown in SEQ ID NO:12. Therapeutic compositions for increasing polynucleotide expression comprise an expression construct containing all or a portion of the polynucleotide sequence as shown in SEQ ID NO:12. Within an expression construct, the polynucleotide segment is oriented in the sense direction and is located downstream from the promoter. Transcription of the polynucleotide segment initiates at the promoter. The expression construct can be introduced into cells along with a pharmaceutically acceptable carrier to decrease the growth rate of cancer cells or ameliorate other abnormal characteristics. Expression of the polynucleotide sequence can be monitored by detecting production of mRNA which hybridizes to the delivered polynucleotide or by detecting protein encoded by the delivered polynucleotide.

Proteins that are expressed from the polynucleotide sequences of the invention can be produced recombinantly in prokaryotic or eukaryotic host cells, such as bacteria, yeast, insect, or mammalian cells, using expression vectors known in the art. Enzymes can be used to generate less than full length polypeptides by enzymatic proteolysis of full-length proteins of the invention. Alternatively, synthetic chemistry methods, such as solid-phase peptide synthesis, can be used to synthesize the proteins and polypeptides.

Species homologs of human subgenomic polynucleotides or the encoded polypeptides can be identified by making suitable probes or primers and screening cDNA expression libraries from other species, such as mice, monkeys, yeast, or bacteria. Mammalian homologs are preferred, however Proteins or polypeptides expressed from the polynucleotide sequences as shown in SEQ ID NO:1-15 can be isolated and purified from human cells that express the proteins. The proteins can be obtained substantially free from other human proteins by standard protein purification methods, such as size exclusion chromatography, ion exchange chromatography, ammonium sulfate fractionation, affinity chromatography, or preparative gel electrophoresis Proteins or polypeptides expressed from the polynucleotides of the invention can also be used in a fusion protein, for example, as an immunogen. The fusion protein comprises two protein segments. The first protein segment consists of at least six, eight, ten, twelve, fifteen, twenty or thirty contiguous amino acids of a polypeptide sequence expressed from a polynucleotide sequence as shown in SEQ ID NOs:1-15. The first protein segment is fused to a second protein segment by means of a peptide bond. The second protein segment can be a full-length protein or a fragment of a protein. Techniques for making fusion proteins, either recombinantly or by covalently linking two protein segments, are well known in the art.

The second protein or protein fragment of a fusion protein can be derived from another type of protein or a similar protein. The second protein or protein fragment can be labeled with a detectable marker, such as a radioactive or fluorescent tag, or can be an enzyme that will generate a detectable product. Enzymes suitable for this purpose, such as β-galactosidase, are well-known in the art. A fusion protein can be used, for example, to target the proteins of the invention or polypeptides to a particular location in a cell or tissue, in various assays, such as the yeast two-hybrid technique, or as an immunogen.

The proteins or polypeptides expressed from the polynucleotides of the invention can be used for generating antibodies. The antibodies can be used, inter alia, to detect and quantitate expression of the cognate protein. Proteins or polypeptides expressed from the polynucleotides of the invention comprising at least six, eight, ten, twelve, fifteen, twenty or thirty consecutive amino acids can be used as immunogens. The proteins or polypeptides can be used to obtain a preparation of antibodies which specifically bind to a protein or polypeptide of the invention. The antibodies can be polyclonal or monoclonal Techniques for raising both polyclonal and monoclonal antibodies are well known in the art.

Single chain antibodies can also be constructed. Single chain antibodies which specifically bind to a protein or polypeptide expressed from the polynucleotides of the invention can be isolated, for example, from single-chain immunoglobulin display libraries, as are known in the art. The library is "panned" against a protein or polypeptide, and a number of single chain antibodies which bind different epitopes of the polypeptide with high-affinity can be isolated. Hayashi et al., 1995, *Gene* 160:129-30. Such libraries are known and available to those in the art. The-antibodies can also be constructed using the polymerase chain reaction (PCR), using hybridoma cDNA as a template. Thirion et al., 1996, *Eur. J. Cancer Prev.* 5: 507-11.

The single chain antibody can be mono- or bi-specific, and can be bivalent or tetravalent. Construction of tetravalent bispecific single chain antibodies is taught in Coloma and Morrison, 1997, *Nat. Biotechnol.* 15:159-63 Construction of bivalent bispecific single chain antibodies is taught in Mallender and Voss, 1994, *J. Biol. Chem.* 269:199-206.

A nucleotide sequence encoding the single chain antibody can then be constructed using manual or automated nucleotide synthesis, cloned into DNA expression vectors using standard recombinant DNA methodologies, and introduced into cells which express the selected gene, as described below. Alternatively, the antibodies can be produced directly using filamentous phage technology. Verhaar et al., 1995, *Int. J. Cancer* 61:497-501, Nicholls et al., 1993, *J. Immunol. Meth.* 165:81-91.

The antibodies bind specifically to the epitopes of the proteins or polypeptides expressed from the polynucleotides of the invention. In a preferred embodiment, the epitopes are not present on other human proteins. Typically a minimum number of contiguous amino acids to encode an epitope is 6, 8, or 10. However, more can be used, for example, at least 15, 25, or 50, especially to form epitopes which involve non-contiguous residues or particular conformations Antibodies that bind specifically to the proteins or polypeptides include those that bind to full-length proteins or polypeptides. Specific binding antibodies do not detect other proteins on Western blots of human cells, or provide a signal at least ten-fold lower than the signal provided by the target protein of the invention. Antibodies which have such specificity can be obtained by routine screening. In a preferred embodiment of the invention, the antibodies immunoprecipitate the proteins or polypeptides expressed from the polynucleotides of the invention from cell extracts or solution. Additionally, the antibodies can react with proteins or polypeptides expressed from the polynucleotides of the invention in tissue sections or on Western blots of polyacrylamide gels. Preferably the antibodies do not exhibit nonspecific cross-reactivity with other human proteins on Western blots or in immunocytochemical assays.

Techniques for purifying antibodies to the proteins or polypeptides expressed from the polynucleotides of the invention are available in the art. In a preferred embodiment, the antibodies are passed over a column to which a particular protein or polypeptide expressed from the polynucleotides of the invention is bound. The bound antibodies are then eluted, for example, with a buffer having a high salt concentration.

Therapeutic compositions of the invention also comprise a pharmaceutically acceptable carrier. Pharmaceutically acceptable carriers are well known to those in the art. Such carriers include, but are not limited to, large, slowly metabolized macromolecule, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates.

Therapeutic compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for the therapeutic composition.

Typically, a therapeutic composition is prepared as an injectable, either as a liquid solution or suspension, however, solid forms suitable for solution in, or suspension in, liquid vehicles prior to injection can also be prepared, A composition can also be formulated into an enteric coated tablet or gel capsule according to known methods in the art, such as those described in U.S. Pat. No. 4,853,230, EP 225,189, AU 9,224, 296, and AU 9,230,801.

Administration of the therapeutic agents of the invention can include local or systemic administration, including injection, oral administration, particle gun, or catheterized administration, and topical administration. Various methods can be used to administer a therapeutic composition directly to a specific site in the body.

For treatment of tumors, for example a small tumor or metastatic lesion can be located and a therapeutic composition injected several times in several different locations within the body of the tumor. Alternatively, arteries which serve a tumor can be identified, and a therapeutic composition injected into such an artery, in order to deliver the composition directly into the tumor.

A tumor which has a necrotic center can be aspirated and the composition injected directly into the now empty center of the tumor. A therapeutic composition can be directly administered to the surface of a tumor, for example, by topical application of the composition. X-ray imaging can be used to assist in certain of the above delivery methods. Combination therapeutic agents, including a protein or polypeptide or a subgenomic polynucleotide and other therapeutic agents, can be administered simultaneously or sequentially.

Receptor-mediated targeted delivery can be used to deliver therapeutic compositions containing subgenomic polynucleotides, proteins or reagents such as antibodies, ribozymes, or antisense oligonucleotides of the invention to specific tissues. Receptor-mediated delivery techniques are described in, for example, Findeis et al. (1993), *Trends in Biotechnol.* 11, 202-05, Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621-24, Wu et al. (1994), *J. Biol. Chem.* 269, 542-46; Zenke et al. (1990), *Proc. Natl. Acad. Sci. U.S.A.* 87, 3655-59; Wu et al. (1991), *J. Biol. Chem.* 266, 338-42.

Alternatively, therapeutic compositions can be introduced into human cells ex viva, and the cells then replaced into the human. Cells can be removed from a variety of locations including, for example, from a selected tumor or from an affected organ. In addition, a therapeutic composition can be inserted into non-affected, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with a therapeutic composition utilizing any of the above-described techniques, followed by the return of the cells to the human, preferably to-or within the vicinity of a tumor or other site to be treated. The methods described above can additionally comprise the steps of depleting fibroblasts or other non-contaminating tumor cells subsequent to removing tumor cells from a human, and/or the step of inactivating the cells, for example, by irradiation.

Both the dose of a composition and the means of administration can be determined based on the specific qualities of the therapeutic composition, the condition, age, and weight of the patient, the progression of the disease, and other relevant factors. Preferably, a therapeutic composition of the invention increases or decreases expression of a polynucleotide by 50%, 60%, 70%, or 80%. Most preferably, expression of the polynucleotide is increased or decreased by 90%, 95%, 99%, or 100%. The effectiveness of the mechanism chosen to alter expression of the polynucleotide can be assessed using methods well known in the art, such as hybridization of nucleotide probes to mRNA of the polynucleotide, quantitative RT-PCR, or detection of a protein or polypeptide using specific antibodies.

If the composition contains protein, polypeptide, or antibody, effective dosages of the composition are in the range of about 5 μg to about 50 μg/kg of patient body weight, about 50 μg to about 5 mg/kg, about 100 μg to about 500 μg/kg of patient body weight, and about 200 to about 250 μ/kg Therapeutic compositions containing subgenomic polynucleotides can be administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action and efficacy of transformation and expression are considerations that will effect the dosage required for ultimate efficacy of the subgenomic polynucleotides. Where greater expression is desired over a larger area of tissue, larger amounts of subgenomic polynucleotides or the same amounts re-administered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

The therapeutic compositions are useful in treating pancreatic cancer and pancreatic dysplasia, as well as other types of cancers such as: bone cancer; brain tumors; breast cancer; endocrine system cancers, such as cancers of the thyroid, pituitary, and adrenal glands and the pancreatic islets; gastrointestinal cancers, such as cancer of the anus, colon, esophagus, gallbladder, stomach, liver, and rectum; genitourinary cancers such as cancer of the penis, prostate and testes; gynecological cancers, such as cancer of the ovaries, cervix, endometrium, uterus, fallopian tubes, vagina, and vulva, head and neck cancers, such as hypopharyngeal, laryngeal, oropharyngeal cancers, lip, mouth and oral cancers, cancer of the salivary gland, cancer of the aerodigestive tract and sinus cancer, leukemia; lymphomas including Hodgkin's and non-Hodgkin's lymphoma; metastatic cancer, myelomas; sarcomas; skin cancer, urinary tract cancers including bladder, kidney and urethral cancers; and pediatric cancers, such as pediatric brain tumors, leukemia, lymphomas, sarcomas, liver cancer and neuroblastoma and retinoblastoma.

The following example provides data and experimental procedures. However, the invention is not limited to the example. The invention is defined in the specification as a whole which includes the claims.

EXAMPLE 1

A family was identified that had -several members who had been diagnosed with pancreatic cancer. The pathological features of disease in the family included progression from normal to metaplasia to dysplasia to cancer. Tissues were obtained from a member of the family diagnosed with pancreatic cancer, from a member of the family diagnosed with dysplasia of pancreatic cells, from a person unrelated to the family diagnosed with pancreatitis, and, from a person unrelated to the family with a normal pancreas.

Ductal cells from the tissues of each of these subjects were cultured and mRNA was isolated from the cultures. The mRNA was subjected to reverse transcriptase polymerase chain reaction using 200 primer pairs (10 anchored and 20 arbitrary primers). The resulting cDNA was subjected to a differential display in which the cDNA from each of the 4 samples were compared on a gel. Bands of cDNA that appeared to be up- or down-regulated in the dysplastic or pancreatic cancer samples, as compared to the normal and pancreatitis samples, were cut from the gel, amplified, cloned, and sequenced.

The following polynucleotides sequences, as shown in SEQ ID NOS: 1-15, were identified as being mis-regulated in pancreatic cancer or dysplasia or both:

TABLE 1

Up-Regulated and Down-Regulated Polynucleotides in Pancreatic Cancer and Dysplasia

| SEQ ID NO. | Regulation Status |
| --- | --- |
| SEQ ID NO: 1 | Up in dysplasia only |
| SEQ ID NO: 2 | Up in dysplasia and cancer |
| SEQ ID NO: 3 | Up in dysplasia only |
| SEQ ID NO: 4 | Up in dysplasia only |
| SEQ ID NO: 5 | Up in dysplasia and cancer |
| SEQ ID NO: 6 | Up in dysplasia only |
| SEQ ID NO: 7 | Up in dysplasia only |
| SEQ ID NO: 8 | Up in dysplasia only |
| SEQ ID NO: 9 | Up in dysplasia only |
| SEQ ID NO: 10 | Up in dysplasia only |
| SEQ ID NO: 11 | Up in dysplasia only |
| SEQ ID NO: 12 | Down in cancer only |
| SEQ ID NO: 13 | Up in dysplasia only |
| SEQ ID NO: 14 | Up in dysplasia only |
| SEQ ID NO: 15 | Up in dysplasia and cancer |

All patents, published patent applications and publications cited herein are incorporated by reference as if set forth fully herein.

Although certain preferred embodiments have been described herein, it is not intended that such embodiments be construed as limitations on the scope of the invention except as set forth in the following claims.

I claim:

1. An isolated subgenomic polynucleotide comprising at least twelve contiguous nucleotides of SEQ ID NO:5, or the full complement of said at least twelve contiguous nucleotides of SEQ ID NO:5.

2. The isolated subgenomic polynucleotide of claim 1 comprising at least eighteen contiguous nucleotides of SEQ ID NO:5.

3. An isolated nucleotide probe comprising at least twenty-five contiguous nucleotides of SEQ ID NO:5, or the full complement of said at least twenty-five contiguous nucleotides of SEQ ID NO:5.

4. The isolated nucleotide probe of claim 3 wherein said probe comprises at least fifty contiguous nucleotides of SEQ ID NO:5.

5. A method of diagnosing cancer in a patient comprising determining the amount of a first set of mRNA molecules in a patient sample and in a normal sample, wherein said mRNA molecules of said first set are complementary to the minus strand of a double-stranded polynucleotide sequence, wherein said double-stranded polynucleotide sequence is selected from the group of polynucleotides as shown in SEQ ID NOs:1, 3-4, 6-11, and 13-14; determining the amount of a second set of mRNA molecules in the patient sample and in the normal sample, wherein said mRNA molecules of said second set are complementary to the minus strand of a double-stranded sequence, wherein said double-stranded polynucleotide sequence is SEQ ID NO: 5; and comparing the determined amounts; wherein a patient sample which contains more of the second set of mRNA molecules than the normal sample and which contains substantially the same amount of the first set of mRNA molecules, as compared to the normal sample, is identified as cancerous.

6. An isolated nucleic acid molecule comprising a polynucleotide sequence selected from the group consisting of (a) the polynucleotide sequence of SEQ ID NO: 5; and (b) a polynucleotide sequence fully complementary to (a).

7. An isolated nucleic acid molecule comprising a polynucleotide sequence encoding a polypeptide encoded for by SEQ ID NO:5, or the full complement thereof.

8. A method of diagnosing cancer in a patient comprising comparing the amount of mRNA molecules in a patient sample and in a normal sample, wherein said mRNA molecules are complementary to the polynucleotide sequence of SEQ ID NO:5, or a naturally occurring variant of SEQ ID NO:5, wherein said naturally occurring variant hybridizes to SEQ ID NO:5 under conditions including a wash in 2×SCC, 0.1% SDS at 50° C. for 20 minutes, or the complement of SEQ ID NO:5 or said naturally occurring variant of SEQ ID NO:5, wherein a patient sample containing more of said mRNA molecules than the normal sample is identified as cancerous and wherein the expression profile of the mRNA molecules is the same as for SEQ ID NO:5.

9. The method of claim 8 wherein the cancer is pancreatic cancer.

* * * * *

SEQUENCE LISTING

```
<160> NUMBER OF SEQ ID NOS: 15

<210> SEQ ID NO 1
<211> LENGTH: 492
<212> TYPE: DNA
<213> ORGANISM: Homo sapien

<400> SEQUENCE: 1
atgaactcgg tttaagacag ggcttcttca ccattgcgag agcgttcacc gggacgagtg      60
gcaagagtct tggcttggat agcatgaaga gccccagtac aaggaagaat actggaaatg     120
ctcaattcgt ggagcgcgtt taaacgacga tttatttggt tttcaatgac cgaggactta     180
tgacaggatg attacatttg accttgggac atgaacgctt ggactgctga cttgtgtgta     240
aagctgtttt gtttgtttgt gtcttgcttg acagtggttc tcgatcatgg tgatacctga     300
```

```
tgctttggac atgtccactt actcctctat tattcgttgg atcattgttt attctgatag    360
atagtgactt atgttcggat gtcgatcaca ggattgtgat tgttagtcca ctgtatctct    420
gatcgaatag gtctatatat tattatttag atagaaaaag tagcaatcca cttaggagat    480
ttattgatct gc                                                        492

<210> SEQ ID NO 2
<211> LENGTH: 545
<212> TYPE: DNA
<213> ORGANISM: Homo sapien

<400> SEQUENCE: 2
tcaggtttga ggctggaaaa agaatcatcc cttcctttcg agttgagatt gtttctcatt     60
ttataagtag cttttatttt atttgaaatt tgaatttctc ttaaaatggt agagtatacc    120
aactttacag aaaggggaaa aaagtcacct actgactgaa cacagctttt accaatttga    180
gcgtctcctt gcagtctttt gaaatacgta tatgggttac accattgtaa acatgtgttc    240
agagcttgca attcataaat atgtttatgt ccgttatcta atgtgagctc aaaacacaat    300
aagagggtca gggttgtgaa gaaggcagga caggaattat ttaacccatt tttcaaatga    360
gaaaactgtg gcccagatac agaatgtcac ttgctaaaat cacatacatt gaaaccagtt    420
ctctccagca tgtcacagtg cttctgtgtt agagcccaag ttacaaacca aagtgtacaa    480
gggcacagat tattagcaat ttacatttaa aaattttat atttcctaac tgatacatat    540
taatt                                                               545

<210> SEQ ID NO 3
<211> LENGTH: 978
<212> TYPE: DNA
<213> ORGANISM: Homo sapien

<400> SEQUENCE: 3
gtaggtgttg tatttctact ttacaggtag gaaaatggag gctaagaaaa gttaatttgt     60
ccgagggccc tctgatgata gtgaaactgg gatggaacct ctgcctgctt gcttctgagg    120
tctgggctcc taactactgc tctactgcct cgagccaaga gatttacgcc ctattaagca    180
atttgttgtg cgataaattg gaagacacag cagataagca aacaactcaa gcaaccaggt    240
cggttcctgg agtttctgaa ttgttgggac caaggggccg tgcagaggta accacagctg    300
gcgtagtgtg gttgaggtag ccctattagc cttttagttg ctgttactaa tttatttctc    360
agtggtcaat gaaccaattg gccatcaatc agctttgtgt ataggtcatg ctcccatggc    420
tctgacccag gttgctgctc agagttggca tcgtggctaa atattacta gaggtcaaag    480 atatgtgtgt gtttgtggtt gatttagtcg agtgatctag aggaatctga accttagaga    540
ctgaagaaga accagcattt ctgggcaata atacttgagt taaggagagt gtagcaaaac    600
tctaggttag cattggcagt ccctaggatt cagactgtag gcctaaatga ccctcagtcc    660
agagctgtac ctaatgagga caatacattt taatgtgagt ccattcttaa cagcaaaatt    720
tcctctttgc ttgtcaccag ggaaaaatgg gtttgcatag aaaaggtgga gattgagggg    780
gaagcagaat ggacaaggag taagaggga atccaactac ttagatttga gctttcgttc    840 ttcttttggta gttgtagagg tgagcttacc aaagcataga tgacaggcaa tgtggtatac    900
aagttactac actccaaaag tctgggggttc ttacttattt tgtgcatgac atccaaagta    960
gcctaataaa atctttc                                                  978
```

<210> SEQ ID NO 4
<211> LENGTH: 978
<212> TYPE: DNA
<213> ORGANISM: Homo sapien

<400> SEQUENCE: 4

| gtagatgttg tatttctact ttacaggtag gaaaatggag gctaagaaaa gttaatttgt | 60 |
| ccgagggccc tctgatgata gtgaaactgg gatggaacct ctgcctgctt gcttctgagg | 120 |
| tctgggctcc taactactgc tctactgcct cgagccaaga gatttacgcc ctattaagca | 180 |
| atttgttgtg cgataaattg gaagacacag cagataagca aacaactcaa gcaaccaggt | 240 |
| cagttcctgg agtttctgaa ttgttgggac caagggggccg tgcagaggta accacagctg | 300 |
| gcgtagtgtg gttgaggtag ccctattagc cttttagttg ctgttactaa tttatttctc | 360 |
| agtggtcaat gaaccaattg ccatcaatc agctttgtgt ataggtcatg ttcccatggc | 420 |
| tctgacccag gttgctgctc agagttggca tcgtggctaa atattacta gaggtcaaag | 480 |
| atatgtgtgt gtttgtggtt gatttagtcg agtgatctag aggaatctga accttagaga | 540 |
| ctgaagaaga accagcattt ctgggcaata atacttgagt taaggagagt gtagcaaaac | 600 |
| tctaggttag cattggcagt ccctaggatt cagactgtag gcctaaatga ccctcagtcc | 660 |
| agagctgtac ctaatgagga caatacattt taatgtgagt ccattcttaa cagcaaaatt | 720 |
| tcctctttgc ttgtcaccag ggaaaaatgg gtttgcatag aaaaggtgga gattgagggg | 780 |
| gaagcagaat ggacaaggag taaagaggga atccaactac ttagatttga gctttcgttc | 840 |
| ttctttggta gttgtagagg tgagcttacc aaagcataga tgacaggcaa tgtggtatac | 900 |
| aagttactac actccaaaag tctggggttc ttacttattt tgtgcatgac atccaaagta | 960 |
| gcctaataaa atctttttc | 978 |

<210> SEQ ID NO 5
<211> LENGTH: 539
<212> TYPE: DNA
<213> ORGANISM: Homo sapien

<400> SEQUENCE: 5

| aatagacatt atactttcta tgtgtggaaa agagttttc aaagatatga aactgtaaaa | 60 |
| tatttgttag ttccagccta tatttgct ggttggagta tagctgactc attgaaatca | 120 |
| aagtcaattt tttggaattt aatgtttttc atatgcttgt tcactgttat agttcctcag | 180 |
| aaactgctgg aatttcgtta cttcatttta ccttatgtca tttataggct taacatacct | 240 |
| ctgcctccca catccagact catttgtgaa ctgagctgct atgcagttgt taatttcata | 300 |
| acttttttca tctttctgaa caagactttt cagtggccaa atagtcagga cattcaaagg | 360 |
| tttatgtggt aatatcagtg atatttcgaa ctgtgaaaat ggacttaata attagaccat | 420 |
| ttctacaaag aacaactgaa taggtggaaa acatggaatt tcttttaggt gcagtggtgg | 480 |
| tcttcaaatt acattagttt ttttatata tattttaaac atatgtaaga aattaagtg | 539 |

<210> SEQ ID NO 6
<211> LENGTH: 491
<212> TYPE: DNA
<213> ORGANISM: Homo sapien

<400> SEQUENCE: 6

| atgaactcgg tttaagacag ggcttcttca ccattgcgag aacgttcacc gggacgagtg | 60 |
| gcaagagtct tggcttggat agcatgaaga gccccagtac aaggaagaat actggaaatg | 120 |

```
ctcaattcgt ggagcgcgtt taaacgacga tttatttggt tttcaatgac cgaggactta      180
tgacaggatg attacatttg accttgggac atgaacgctt ggactgctga cttgtgtgta      240
aagctgtttg tttgtttgtg tcttgcttga cagtggttct cgatcatgat gatacctgat      300
gctttggaca tgtccactta ctcctctatt attcgttgga tcattgttta ttctgataga      360
tagtgactta tgttcggatg tcgatcacag gattgtgatt gttagtccac tgtatctctg      420
atcgaatagg tctatatatt attatttaga tagaaaagt agcaatccac ttaggagatt       480
tattgatctg c                                                           491

<210> SEQ ID NO 7
<211> LENGTH: 491
<212> TYPE: DNA
<213> ORGANISM: Homo sapien

<400> SEQUENCE: 7
atgaactcgg tttaagacag ggcttcttca ccattgcgag aacgttcacc gggacgagtg       60
gcaagagtct tggcttggat agcatgaaga gccccagtac aaggaagaat actggaaatg      120
ctcaattcgt ggagcgcgtt taaacgacga tttatttggt tttcaatgac cgagacttat      180
gacaggatga ttacatttga ccttgggaca tgaacgcttg gactgctgac ttgtgtgtaa      240
agctgttttg tttgtttgtg tcttgcttga cagtggttct cgatcatgat gatacctgat      300
gctttggaca tgtccactta ctcctctatt attcgttgga tcattgttta ttctgataga      360
tagtgactta tgttcggatg tcgatcacag gattgtgatt gttagtccac tgtatctctg      420
atcgaatagg tctatatatt attatttaga tagaaaagt agcaatccac ttaggagatt       480
tattgatctg c                                                           491

<210> SEQ ID NO 8
<211> LENGTH: 492
<212> TYPE: DNA
<213> ORGANISM: Homo sapien

<400> SEQUENCE: 8
gcagatcaat aaatctccta agtggattgc tactttttct atctaaataa taatatatag       60
acctattcga tcagagatac agtggactaa caatcacaat cctgtgatcg acatccgaac      120
ataagtcact atctatcaga ataaacaatg atccaacgaa taatagagga gtaagtggac      180
atgtccaaag catcaggtat catcatgatc gagaaccact gtcaagcaag acacaaacaa      240
acaaaacagc tttacacaca agtcagcagt ccaagcgttc atgtcccaag gtcaaatgta      300
atcatcctgt cataagtcct cggtcattga aaccaaata atcgtcgtt taaacgcgct        360 ccacgaattg agcatttcca gtattcttcc ttgtactggg gctcttcatg ctatccaagc      420
caagactctt gccactcgtc ccggtgaacg ttctcgcaat ggtgaagaag ccctgtctta      480
aaccgagttc at                                                          492

<210> SEQ ID NO 9
<211> LENGTH: 492
<212> TYPE: DNA
<213> ORGANISM: Homo sapien

<400> SEQUENCE: 9
atgaactcgg tttaagacag ggcttcttca ccattgcgag aacgttcacc gggacgagtg       60
gcaagagtct tggcttggat agcatgaaga gccccagtac aaggaagaat actggaaatg      120
ctcaattcgt ggagcgcgtt taaacgacga tttatttggt tttcaatgac cgaggactta     180
```

```
tgacaggatg attacatttg accttgggac atgaacgctt ggactgctga cttgtgtgta    240
aagctgtttt gtttgtttgt gtcttgcttg acagtggttc tcgatcatga tgatacctga    300
tgctttggac atgtccactt actcctctat tattcgttgg atcattgttt attctgatag    360
atagtgactt atgttcggat gtcgatcaca gggttgtgat tgttagtcca ctgtatctct    420
gatcgaatag gtctatatat tattatttag atagaaaaag tagcaatcca cttaggagat    480
ttattgatct gc                                                         492

<210> SEQ ID NO 10
<211> LENGTH: 492
<212> TYPE: DNA
<213> ORGANISM: Homo sapien

<400> SEQUENCE: 10
atgaactcgg tttaagacag ggcttcttca ccattgcgag aacgttcacc gggacgagtg     60
gcaagagtct tggcttggat agcatgaaga gccccagtac aaggaagaat actggaaatg    120
ctcaattcgt ggagcgcgtt taaacgacga tttatttggt tttcaatgac cgaggactta    180
tgacaggatg attacatttg accttgggac atgaacgctt ggactgctga cttgtgtgta    240
aagctgtttt gtttgtttgt gtcttgcttg acagtggttc tcgatcatga tgatacctga    300
tgctttggac atgtccactt actcctctat tattcgttgg atcattgttt attctgatag    360
atagtgactt atgttcggat gtcgatcaca ggattgtgat tgttagtcca ctgtatctct    420
gatcgaatag gtctatatat tattatttag atagaaaaag tagcaatcca cttaggagat    480
ttattgatct gc                                                         492

<210> SEQ ID NO 11
<211> LENGTH: 492
<212> TYPE: DNA
<213> ORGANISM: Homo sapien

<400> SEQUENCE: 11
atgaactcgg tttaagacag ggcttcttca ccattgcgag aacgttcacc gggacgagtg     60
gcaagagtct tggcttggat agcatgaaga gccccagtac aaggaagaat actggagatg    120
ctcaattcgt ggagcgcgtt taaacgacga tttatttggt tttcaatgac cgaggactta    180
tgacaggatg attacatttg accttgggac atgaacgctt ggactgctga cttgtgtgta    240
aagctgtttt gtttgtttgt gtcttgcttg acagtggttc tcgatcatga tgatacctga    300
tgctttggac atgtccactt actccctat tattcgttgg atcattgttt attctgatag     360
atagtgactt atgttcggat gtcgatcaca ggattgtgat tgttagtcca ctgtatctct    420
gatcgaatag gtctatatat tattatttag atagaaaaag tagcaatcca cttaggagat    480
ttattgatct gc                                                         492

<210> SEQ ID NO 12
<211> LENGTH: 826
<212> TYPE: DNA
<213> ORGANISM: Homo sapien

<400> SEQUENCE: 12
tttaggcttc tgcagggggac tctgtacatg tgcgttggca ttatggatcg attttttacag   60 gttcagccag tttcccggaa gaagcttcaa ttagttggga ttactgctct gctcttggcc    120
tccaagtatg aggagatgtt ttctccaaat attgaagact tgtttacat cacagacaat     180 gcttatacca gttcccaaat ccgagaaatg gaaactctaa ttttgaaaga atcgaaattt    240
```

| | |
|---|---:|
| gagttgggtc gacccttgcc actacacttc ttaaggcgag catcaaaagc cggggaggtt | 300 |
| gatgttgaac agcacacttt agccaagtat ttgatggagc tgactctcat cgactatgat | 360 |
| atggtgcatt atcatccttc taaggtagca gcagctgctt cctgcttgtc tcagaaggtt | 420 |
| ctaggacaag gaaaatggaa cttaaagcag cagtattaca caggatacac agagaatgaa | 480 |
| gtattggaag tcatgcagca catggccaag aatgtggtga agtaaatga aaacttaact | 540 |
| aaattcatcg ccatcaagaa taagtatgca agcagcaaac tcctgaagat cagcatgatc | 600 |
| cctcagctga actcaaaagc cgtcaaagac cttgcctctc cactgatagg aaggtcctag | 660 |
| gctgccgtgg cccctgggga tgtgtgcttc attgtgccct ttttcttatt ggtttagaac | 720 |
| tcttgatttt gtacatagtc ctctggtcta tctcatgaaa cctcttctca gaccagtttt | 780 |
| ctaaacatat attgaggaaa aataaagcga ttggtttttc ttaagg | 826 |

<210> SEQ ID NO 13
<211> LENGTH: 819
<212> TYPE: DNA
<213> ORGANISM: Homo sapien

<400> SEQUENCE: 13

| | |
|---|---:|
| ctggagagaa aacccataaa tgccccgaat gtgggagagc cttttttat cagtcattcc | 60 |
| ttatgagaca tatgaaaatt cacactggag agaaaccgta tgaatgtggg aaatgtggga | 120 |
| aagcctttag atattcctta caccttaata acatttaag aaagcatgtt gtgcagaaga | 180 |
| agccctacga atgtgaagaa tgtgggaaag tcattcggga gtcctcaaaa tatacacata | 240 |
| taaggagcca cactggagag aaaccctata atgtaagac atgtggaaaa gactttgcaa | 300 |
| agtcgccagg acttaaaaaa catcttaaga ctcacaaaga tgagaagccc tgtgaatgaa | 360 |
| aggaaggtgg aaaatttttc attaattttc tgactgtacc aaacatgtga ggaggacata | 420 |
| ttggaaggga gctcaagggg ttagcatgag tgagaacatc ttccctgaac tctcgtatct | 480 |
| tacagaaatg tgaaaaaaaa ccctgtgaag gtaaagtcta cagaaagcct ttcatcttca | 540 |
| ttcatcttga gtagacattt gttctcaccc tggagagaaa ctgcgaatct aaaaggaata | 600 |
| tgacaaagcc ttcagcgtgg tctcaaattc atggttcata caagaactca cactgcagag | 660 |
| actccttacg gaataaaaa atgtaggaaa gacctgccgg ccgcggtggc tcatgcctgt | 720 |
| aatcccagca ctttgggagg ccgaggcggg cggatcacga ggtcaggaga tcaagaccat | 780 |
| cctggctaac acggtgatac cccgtctcta ctaaaaata | 819 |

<210> SEQ ID NO 14
<211> LENGTH: 1386
<212> TYPE: DNA
<213> ORGANISM: Homo sapien

<400> SEQUENCE: 14

| | |
|---|---:|
| gtagatgttg tatttctact ttacaggtag gaaaatggag gctaagaaaa gttaatttgt | 60 |
| ccgagggccc tctgatgata gtgaaactgg gatggaacct ctgcctgctt gcttctgagg | 120 |
| tctgggctcc taactactgc tctactgcct cgagccaaga gatctacgcc ctattaagca | 180 |
| atttgttgtg cgataaattg gaagacacag cagataagca acaactcaa gcaaccaggt | 240 |
| cagttcctgg agtttctgaa ttgttgggac caaggggccg tgcagaggta accacagctg | 300 |
| gcgtagtgtg gttgaggtag ccctattagc cttttagttg ctgttactaa tttatttctc | 360 |
| agtggtcaat gaaccaattg gccatcaatc agctttgtgt ataggtcatg ttcccatggc | 420 |
| tctgacccag gttgctgctc agagttggca tcgtggctaa aatattacta gaggtcaaag | 480 |

```
                                          -continued atatgtgtgt gtttgtggtt gatttagtcg agtgatctag aggaatctga accttagaga      540
ctgaagaaga accagcattt ctgggcaata atacttgagt taaggagagt gtagcaaaac      600
tctaggttag cattggcagt ccctagaatt cagactgtag gcctaaatga ccctcagtcc      660
agagctgtac ctaatgagga caatacattt taatgtgagt ccattcttaa cagcaaaatt      720
tcctctttgc ttgtcaccag ggaaaaatgg gtttgcatag aaaaggtgga gattgagggg      780
gaagcagaat ggacaaggag taaagaggga atccaactac ttagatttga gctttcgttc      840
ttctttggta gttgtagagg tgagcttacc aaagcataga tgacaggcaa tgtggtatac      900
aagttactac actccaaaag tctggggttc ttacttattt tgtgcatgac atccaaagta      960
gcctaataaa atcttttcac agaaaaaaaa gctttacttt cctttgccaa atttttaact     1020
ttttattctg aaataatttc agaattattg aaaaatttag agactaggac aacccagatt     1080
cctcaaatat taacacttta ccacatctgc cttctcattc ctctctatat acataggtgc     1140
atgtgtggtt ttaatgttta tttatataca tatcattatt attttcttaa ctgtttgaga     1200
gtaagttgaa gacatgatgc tccttactct ttaaatactt cagtgtgtat ttcctaaaaa     1260
gcaggccatg ttctacatca tcacagtata attatcaaaa ttgggaaatt aatattaatg     1320
caatactatt tatcaaattt taagatctta ttcaaatttc acttgctggc ctaataatgt     1380
tctttc                                                                1386

<210> SEQ ID NO 15
<211> LENGTH: 547
<212> TYPE: DNA
<213> ORGANISM: Homo sapien

<400> SEQUENCE: 15
aaaagtctgc tttgaggcaa aggtaaccca gaatctccca atgaaagaag gctgcacaga       60
ggtctctctc cttcgagttg ggtggtctgt tgattttttcc cgtccacagc ttggtgaaga      120
tgaattctct tacggtttcg atggacgagg actcaaggca gaaaatggac aatttgagga      180
atttggccag acttttgggg agaatgatgt tattggctgc tttgctaatt ttgagactga      240
agaagtagaa ctttccttct ccaagaatgg agaagaccta ggtgtggcat tctggatcag      300
caaggattcc ctggcagacc gggcccttct accccatgtc ctctgcaaaa attgtgttgt      360
agaattaaac ttcggtcaga aggaggagcc cttcttccca ccaccagaag agtttgtgtt      420
cattcatgct gtgcctgttg aggagcgtgt acgcactgca gtccctccca agaccacaga      480
ggaatgtgag gtgattctga tggtgggact acccggatct ggaaagaccc agtgggcact      540
gaaatat                                                                547
```